(12) United States Patent
Wade

(10) Patent No.: US 8,286,505 B2
(45) Date of Patent: *Oct. 16, 2012

(54) METHOD AND SYSTEM FOR MEASURING FLOW AT PATIENT UTILIZING DIFFERENTIAL FORCE SENSOR

(75) Inventor: Richard Wade, Worthington, OH (US)

(73) Assignee: Honeywell International Inc., Morristown, NJ (US)

( * ) Notice: Subject to any disclaimer, the term of this patent is extended or adjusted under 35 U.S.C. 154(b) by 183 days.

This patent is subject to a terminal disclaimer.

(21) Appl. No.: 12/834,260

(22) Filed: Jul. 12, 2010

(65) Prior Publication Data

US 2010/0274216 A1  Oct. 28, 2010

Related U.S. Application Data

(63) Continuation of application No. 12/364,270, filed on Feb. 20, 2009, now Pat. No. 7,775,127.

(60) Provisional application No. 61/140,295, filed on Dec. 23, 2008.

(51) Int. Cl.
*G01F 1/37* (2006.01)
*A61M 31/00* (2006.01)

(52) U.S. Cl. ............... 73/861.52; 73/861.47; 604/93.01; 604/13; 604/246

(58) Field of Classification Search ................ None
See application file for complete search history.

(56) References Cited

U.S. PATENT DOCUMENTS

| | | | |
|---|---|---|---|
| 4,395,915 A | 8/1983 | Singh | |
| 4,528,855 A | 7/1985 | Singh | |
| 4,932,045 A | 6/1990 | Kasoff et al. | |
| 5,124,960 A | 6/1992 | Miller et al. | |
| 5,136,621 A | 8/1992 | Mitchell et al. | |
| 5,656,785 A | 8/1997 | Trainor et al. | |
| 5,661,245 A | 8/1997 | Svoboda et al. | |
| 6,229,190 B1 | 5/2001 | Bryzek et al. | |
| 6,612,179 B1 | 9/2003 | Kurtz | |
| 7,073,375 B2 | 7/2006 | Parker et al. | |
| 7,296,479 B2 | 11/2007 | Hogeland | |
| 7,320,253 B2 | 1/2008 | Hanazawa et al. | |
| 7,559,252 B2 | 7/2009 | Schadler et al. | |
| 7,775,126 B2 * | 8/2010 | Eckhardt et al. | ........... 73/861.52 |

(Continued)

OTHER PUBLICATIONS

U.S. Appl. No. 12/834,321, filed Jul. 12, 2010.
Kremer et al., "Signal Conditioning Circuits for Sensors Frame ASICs* or Modular Signal Conditioning," 8 pages, Analog Microelectronics, Aug. 2000.

*Primary Examiner* — Harshad R Patel
(74) *Attorney, Agent, or Firm* — Seager Tufte & Wickhem LLC.

(57) ABSTRACT

A fluid delivery system and method for measuring flow at a patient utilizing a differential force sensor in order to precisely control the flow of fluid at very low flow rates. The system includes a fluid line through which a fluid is conveyed to the patient, and a flow controller that selectively varies a rate of flow of the fluid through the fluid line. The differential force sensor can be mounted very close to a point of entry of the fluid into the patient's body. An onboard communications device is controllably coupled to the flow controller and to the force sensor, responds to an output signal, and provides a feedback to the flow controller in a closed-loop process. The system can pump the fluid at a higher frequency until the flow rate is actually reached at the patient and then adjust to the flow rate needed to ensure patient health.

20 Claims, 3 Drawing Sheets

U.S. PATENT DOCUMENTS

| | | | |
|---|---|---|---|
| 7,775,127 B2 * | 8/2010 | Wade | 73/861.52 |
| 8,091,436 B2 * | 1/2012 | Eckhardt et al. | 73/861.52 |
| 2008/0114256 A1 | 5/2008 | Zhang et al. | |
| 2010/0100052 A1 | 4/2010 | Eckhardt et al. | |
| 2010/0160893 A1 | 6/2010 | Wade | |

OTHER PUBLICATIONS

Honeywell, "Force Sensors, FSG and FSL Series," 23 pages, 2003.

Honeywell, "Pressure Sensors, FS01/FS03 Force Sensors," 4 pages, 2003.

* cited by examiner

METHOD AND SYSTEM FOR MEASURING FLOW AT PATIENT UTILIZING DIFFERENTIAL FORCE SENSOR

This application is a continuation of U.S. patent application Ser. No. 12/364,270, filed Feb. 20, 2009, and entitled "METHOD AND SYSTEM FOR MEASURING FLOW AT PATIENT UTILIZING DIFFERENTIAL FORCE SENSOR", which claims the benefit of U.S. Provisional Patent Application Ser. No. 61/140,295, entitled "METHOD AND SYSTEM FOR MEASURING FLOW AT PATIENT UTILIZING DIFFERENTIAL FORCE SENSOR," filed on Dec. 23, 2008, which are incorporated herein by reference.

TECHNICAL FIELD

Embodiments are generally related to sensor methods and systems. Embodiments are also related to differential force sensors. Embodiments additionally relate to differential force sensors utilized in the context of monitoring manual patient injections through a fluid line.

BACKGROUND OF THE INVENTION

A variety of fluid delivery systems have been utilized in the medical field for delivering fluids (e.g., medication, nutrition, saline, etc) to a patient at relatively precise delivery rates. Such fluid delivery systems include various types of infusion pumps to administer medicinal fluids automatically and over extended periods of time. A typical infusion pump delivers the medicinal fluid into a patient's venous system utilizing a delivery channel, which usually includes the use of an administration tube (e.g., a polyvinyl chloride tube, etc.) connected to the patient utilizing some form of a catheter, needle, or the like.

For safety reasons and in order to achieve optimal results, it is desirable to administer the medicinal fluids such as, for example, intravenous (IV) fluids, intermittently and with a frequency as often as multiple times per day and in a controlled manner as prescribed by the physician. Depending on the frequency of administration, the patient is either repeatedly connected to and disconnected from an IV line or is continuously connected to an IV line between administrations. In either case, the intermittent medications are generally administered by trained personnel utilizing predefined procedures that often include a series of manual steps and a large number of disposable supplies. Each manual step in such procedures increases the risks associated with multiple manipulations and entry of IV sites.

Accordingly, it will be apparent that it would be desirable to provide a relatively low cost, low complexity system for the delivery of medicinal fluids. A closed-loop system in which a desired parameter is measured to control the system can provide the required accuracy. For example, in a closed-loop system, it would be preferable to measure flow with a sensor and to control an inexpensive fluid delivery pump based upon the measured flow rate so as to achieve a desired flow rate. The problem associated with such disposable deliverable systems for fluids, however, is that such a systems possesses too much compliance to accurately measure the dynamic flow at very low flow rates. Furthermore, the utilized sensor must be sterilized after use or disposed, which is very costly.

The majority of prior art systems utilize inferred flow measurements at the infusion pump. However, at low flow rates (e.g., ~0.05 ml/hr) the time for the system to overcome the compliance in the disposable tubing (e.g., which can be ~6-10 feet long) can be measured in hours, particularly in the case of a neo-natal patient where the catheter in the patient is an extremely small diameter tube and acts as a flow restrictor. While such systems reflect improvements in the art, they do not control fluid delivery in view of actual flow rates and the time required for the fluid to enter the patient increases. In some circumstances, therefore, such systems may require time ability to deliver fluids over a wide range of delivery rates including very low flow rates. Moreover, conventional manufacturing techniques tend to be expensive and, therefore, are not well suited for use in manufacturing disposable items.

Based on the foregoing, it is believed that a need exists for an improved differential force sensor for monitoring manual injections through the fluid line. A need also exists for an improved fluid delivery system for precisely controlling the flow of the fluid into the patient at very low flow rates and to minimize system compliance.

BRIEF SUMMARY

The following summary is provided to facilitate an understanding of some of the innovative features unique to the embodiments disclosed and is not intended to be a full description. A full appreciation of the various aspects of the embodiments can be gained by taking the entire specification, claims, drawings, and abstract as a whole.

It is, therefore, one aspect of the present invention to provide for an improved differential force sensor apparatus capable of automatically monitoring manual injections through a fluid line.

It is another aspect of the present invention to provide for an improved fluid delivery system for precisely controlling the flow of the fluid into the patient at very low flow rates and to minimize system compliance.

The aforementioned aspects and other objectives and advantages can now be achieved as described herein. A fluid delivery system and method for measuring flow at a patient utilizing a differential force sensor in order to precisely control the flow of fluid into a patient at very low flow rates is disclosed. The system includes a fluid line through which a medicinal fluid is conveyed from a reservoir to the patient. A flow controller is also provided, which can be employed to selectively vary a rate of flow of the medicinal fluid through the fluid line. The differential force sensor can be mounted on the patient and very close to a point of entry of the fluid into the patient's body. An onboard communications device can be controllably coupled to the flow controller and to the differential force sensor that monitors a rate of flow of the medicinal fluid through the fluid line, thereby producing an output signal that is indicative of flow rate and/or other data. The onboard communications device responds to the output signal(s), is capable of providing feedback to the flow controller in a closed-loop process, and is able to achieve the desired rate of infusion of the medicinal fluid into the patient. The system can pump the fluid at a higher frequency until the flow rate is actually attained at the patient and then adjusted to the flow rate required to ensure patient health.

The differential force sensor includes the use of two piezoresistive sense die packaged in close proximity to one another. The differential force sensor and components such as the two (or more) piezoresistive sense die can be packaged utilizing any number of packaging processes. The two piezoresistive sense die configuration can be utilized to measure force exerted on a diaphragm on either side of an orifice. The piezoresistive sense die can be packaged in close proximity to make intimate contact with a diaphragm(s) located on either side of the orifice.

The differential force sensor further includes one or more plungers that are capable of making intimate contact with the diaphragm and transferring the force to the piezoresistive sense die. The differential force sensor can be mounted very close to the point of entry into the patient's body. Such differential force sensor is capable of monitoring manual injections through the fluid line. The output of the sensor can be the individual force measurements in the form of an electrical signal (either digital or analog) and potentially a differential signal (the difference between the two sense elements). Additionally, one or more ASIC components and microcontrollers can be utilized to provide thermal calibration and differential calculation.

BRIEF DESCRIPTION OF THE DRAWINGS

The accompanying figures, in which like reference numerals refer to identical or functionally-similar elements throughout the separate views and which are incorporated in and form a part of the specification, further illustrate the embodiments and, together with the detailed description, serve to explain the embodiments disclosed herein.

DETAILED DESCRIPTION

The particular values and configurations discussed in these non-limiting examples can be varied and are cited merely to illustrate at least one embodiment and are not intended to limit the scope thereof.

Figure 1:
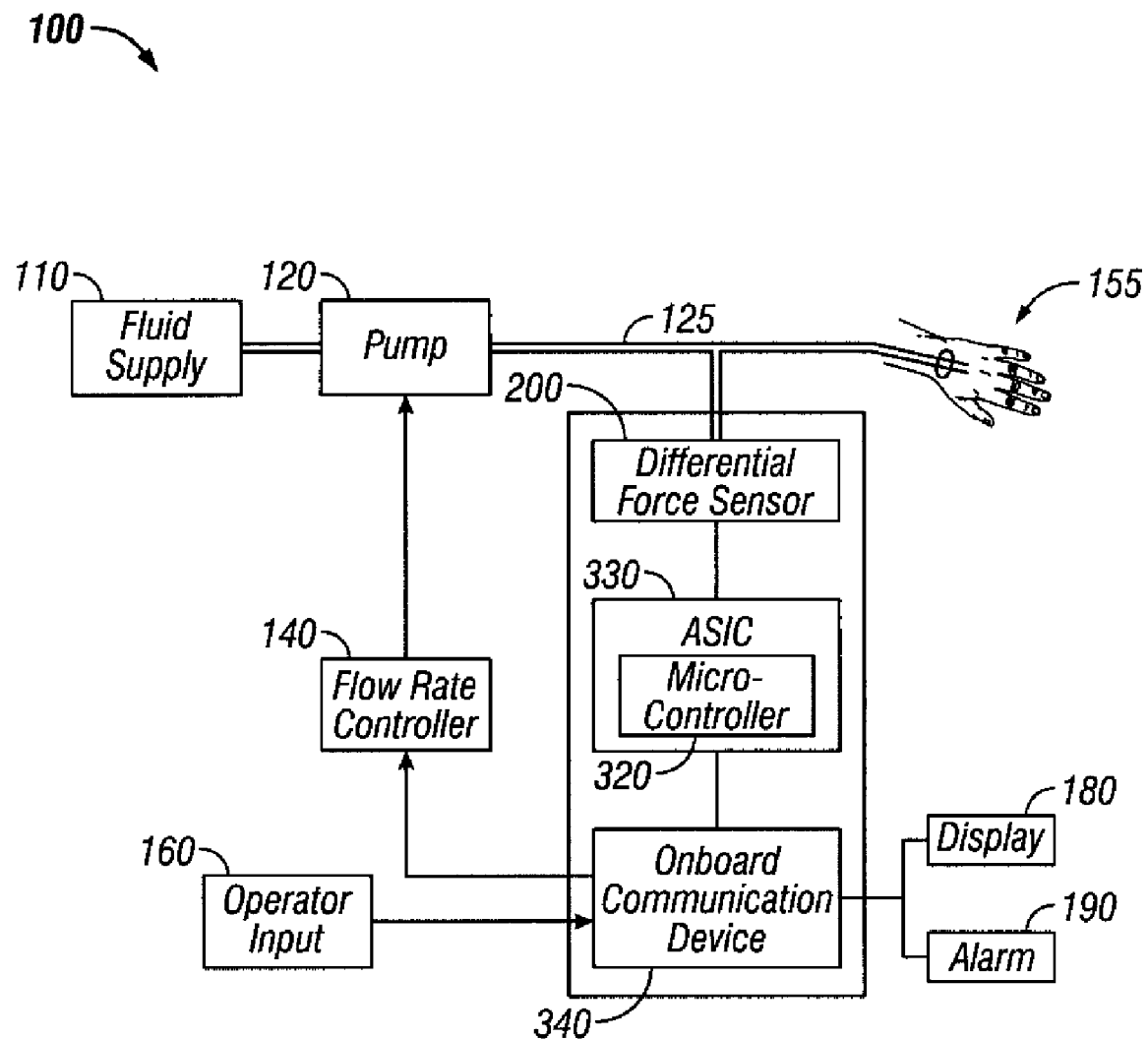
FIG. 1 illustrates a block diagram of a fluid delivery system comprising a differential force sensor, in accordance with a preferred embodiment.

FIG. 1 illustrates a block diagram of a fluid delivery system 100 that includes a differential force sensor 200, in accordance with a preferred embodiment. The fluid delivery system 100 includes a fluid supply 110 of any desired parenteral fluid and a pump 120, which may be, for example, a peristaltic pump, to which is connected to a tube 125, which in turn is connected to a cannula inserted into the vein of a patient 155. Note that the embodiments discussed herein should not be construed in any limited sense. It can be appreciated that such embodiments reveal details of the structure of a preferred form necessary for a better understanding of the invention and may be subject to change by skilled persons within the scope of the invention without departing from the concept thereof.

The pressure in the tube 125 can be monitored by the differential force sensor 200, which can be connected to an ASIC 330 for supplying digital data representing the pressure in the tube to a microcontroller 320. Note that some embodiments can utilize one ASIC per sense die and thus utilize two ASIC's capable of communicating the microcontroller 320. The differential force sensor 200 is also capable of monitoring manual injections through the fluid line. The output of the sensor 200 can be the individual force measurements in the form of an electrical signal either digital or analog and potentially a differential signal (i.e., the difference between the two sense elements 240). The ASIC 330 can be utilized to provide linearization and thermal compensation through the implementation of calibration and differential calculation operations. The microcontroller 320 can be utilized to provide a differential calculation or a flow rate calculation and also to communicate with external electronics through an onboard communications device 340.

The microcontroller 320 can be provided as a single integrated circuit chip that contains a processor (e.g., CPU), a non-volatile memory for the program (e.g., ROM or flash), volatile memory for input and output (e.g., RAM), a clock, and an I/O control unit. Microcontroller 320 can thus function as a "computer on a chip".

Note that the term "ASIC" as utilized herein is an acronym for Application Specific Integrated Circuit. ASIC 330 can thus be provided in the form of an integrated circuit chip that is custom designed for a specific application rather than a general-purpose chip such as a microprocessor. ASICs generally improve performance over general-purpose CPUs because ASICs are capable of being "hardwired" to perform a specific job and do not incur the overhead of fetching and interpreting stored instructions. In some embodiments, however, a standard cell ASIC may include one or more microprocessor cores and embedded software, in which case, it may be referred to as a "system on a chip" (SoC). Thus, the ASIC 330 discussed herein may constitute in an alternative embodiment, an SOC.

The microcontroller 320 generally provides one or more output signals to a flow rate controller 140, which controls the rate of flow delivered by the pump 120 through the onboard communications device 340. In some embodiments, the microcontroller 320 can also communicate electronically with an operator display 180 and can generate an alarm signal 190 through the onboard communications device 340. The microcontroller 320 can also be enabled to accept operator input 160 for controlling the rate of flow and the like. In a preferred embodiment, however, the microcontroller 320 communicates with an external device, such as an external operator display 180. In other words, microcontroller 320 can drive external devices, such as display 180. While a microcontroller 320 could be packaged with a display such as display 180 or an alarm such as alarm 190, this would not be practical, because such devices would then hang from the patient's arm or leg. The preferred implementation involves the use of such external devices driven by microcontroller 320.

The differential force sensor 200 can be mounted on the patient and very close to the point of entry into the body for sensing a differential flow of the fluid in the tube 125 and for generating a flow rate signal indicative of a rate of flow of the fluid in the tube 125. The flow rate controller 140 selectively varies a rate of flow of the medicinal fluid through the fluid line. The flow rate controller 140 controls the pump 120 and causes adjustments to the output rate of the pump 120 as a function of the flow rate signal, whereby the desired flow rate is substantially achieved. The onboard communications device 340 can be controllably coupled to the flow controller 140 and to the differential force sensor 200 that monitors the rate of flow of the medicinal fluid through the fluid line, thereby producing an output signal indicative of the rate of fluid flow.

The onboard communications device 340 can respond to the output signal and generate a feedback signal to the flow controller 140 in a closed-loop process, in order to thereby achieve a desired rate of infusion of medicinal fluid into the patient. Note that the onboard communications device 340 may constitute, for example, a USB port capable of communication via any communication protocol and/or other types of high-speed communication devices, depending upon design considerations. Also note that the term "medicinal fluid" as utilized herein can refer to medication, nutrition, saline and/or any other fluid necessary for the health and well-being of a patient receiving such fluid.

Figure 2:
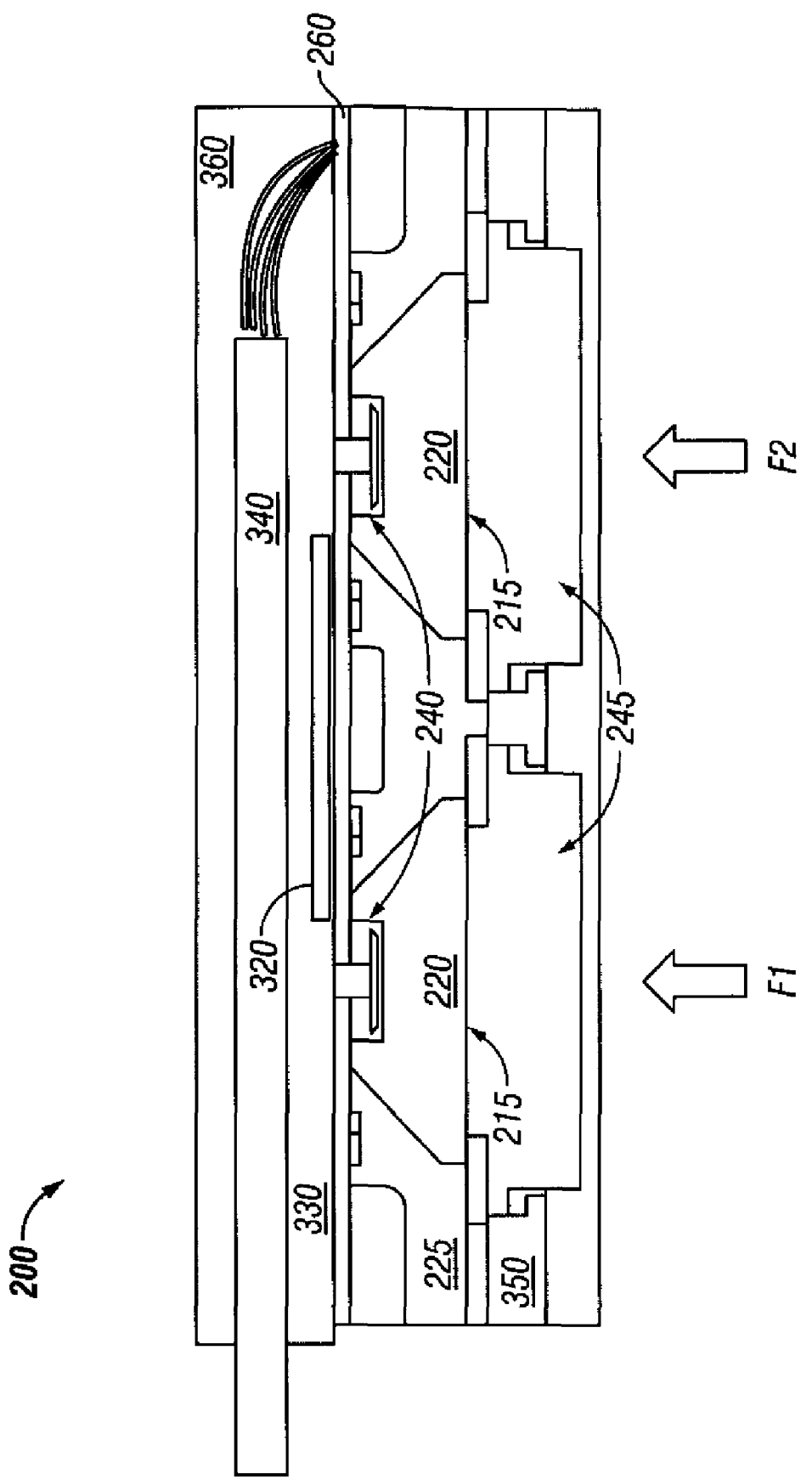
FIG. 2 illustrates a cross-sectional view of the differential force sensor of FIG. 1, in accordance with an alternative embodiment.

FIG. 2 illustrates a cross-sectional view of the differential force sensor 200 of FIG. 1, modified to include two piezoresistive sense die 240 each glued to the PCB 260, in accordance with an alternative embodiment. Note that in FIGS. 1-2, identical or similar parts or elements are generally indicated by identical reference numerals. The differential force sensor 200 depicted in FIG. 1 can be configured to include two piezoresistive sense die 240 that are packaged in close proximity to one another and glued to a PCB (Printed Circuit Board) 260. A molded housing 225 can be positioned over the sense die 240 and the gel 220 dispensed and cured into the orifice 410 (i.e., not shown in FIG. 2, but depicted in FIG. 3) above the sense die 240 so it makes intimate contact with the topside of the sense die 240.

A diaphragm 215 and a plunger 245 can be placed on top of the gel 220. The two piezoresistive sense die 240 can be utilized to measure forces exerted on the diaphragm 215 on either side of the orifice 410. The forces F1 and F2 from the diaphragm 215 can be transmitted through the plungers 245 and into the gel 220 and finally into the piezoresistive sense die 240. The signal compensation for the piezoresistive sense die 240 can be completed through the ASICs 330. The microcontroller 320 can be utilized to communicate with external electronics through the USB cable 340. The differential force sensor 300 can be covered with a bottom cover 350 and a top cover 360.

Note that the embodiments discussed herein should not be construed in any limited sense. It can be appreciated, of course, that other types of packaging processes may also be utilized such as, for example, the sense die glued to the PCB, wherein as a ball bearing makes intimate contact with the sense die diaphragm, the force is transmitted to the ball bearing, and so forth. However, it will be apparent to those skilled in the art that other packaging processes can be utilized as desired without departing from the scope of the invention.

Such differential force sensor 200 is a high-performance transducer specifically designed to address the needs of medical and specialized OEM (Original Equipment Manufacturer) applications. The differential force sensor 200 can be specified to operate with either a constant current or voltage supply. The differential force sensor 300 employs a solid state piezoresistive pressure transducer mounted in a plastic package. Such an approach provides a reliable solution for applications where force can be applied by a flexible membrane to the sensor, such as found in infusion pumps. The differential force sensor 200 is also capable of providing access to important safety features in critical care medical instrumentation, such as occlusion detection or infiltration detection. The pressure data can provide medical personnel with useful diagnostic information regarding the condition of the patient's circulatory system. The differential force sensor 200 can also be utilized with other medical dispensing devices, such as syringe pumps, to improve safety and accuracy.

Figure 3:
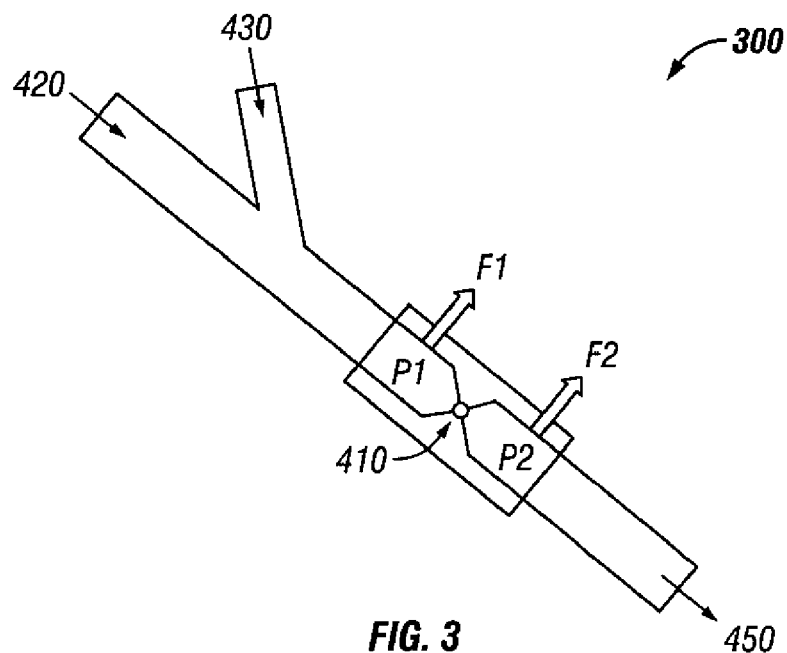
FIG. 3 illustrates a schematic diagram of an intravenous fluid delivery system utilizing the differential force sensor of FIGS. 1-2 on either side of an orifice for monitoring manual injections, in accordance with an alternative embodiment.

FIG. 3 illustrates a schematic diagram of an intravenous fluid delivery system 300 capable of utilizing the differential force sensor 200 shown in FIGS. 1-2 on either side of the orifice 410 for monitoring manual injections, in accordance with an alternative embodiment. Note that in FIGS. 1-3, identical or similar parts or elements are generally indicated by identical reference numerals. The intravenous fluid delivery system 300 depicted in FIG. 3 can be configured to include an intravenous tube 420 and an injection point 430 for delivering medications to a patient, as illustrated by arrow 450. The differential force sensor 200, which includes piezoresistive sense die 240, can be placed on either side of the orifice 410 for measuring differential force on either side of the orifice 410. The piezoresistive sense die 240 can be utilized to measure forces F1 and F2 exerted on the diaphragm 215 on either side of the orifice 410. The piezoresistive sense die 240 can be packaged in close proximity to make intimate contact with the diaphragm(s) 215 located on either side of the orifice 410.

Intravenous medications such as, for example, antibiotics, antivirals, antiemetics, chemotherapy, and biotechnology drugs can be administrated intermittently with a frequency through the injection point 430. The differential force sensor 200 can be mounted very close to the point of entry into the patient's body. The differential force sensor 200 is capable of monitoring manual injections through the intravenous line 420. Such small size and lightweight differential force sensor for monitoring manual injections through the intravenous line 420 reduce patient discomfort.

For example, in delivering medicine to a baby in a critical care environment, the amount of medicine to be delivered is prescribed by the doctor and the medical staff worker gets the medicine into the patient. The sensor 200 can be mounted on the baby very close to the point of entry into the body; hence, the system 300 is capable of avoiding all of the compliance right up to the baby's catheter and the medicine can be into the patient within 10's of minutes, instead of hours. The time from prescription to implementation can also be minimized. Another factor to consider is the concentration of medicine. In some instances, a doctor may prescribe a high concentrated medicine that flows into the patient at very low flow rates and causes the same problem. The system and method disclosed herein can at least ensure that at the system start, fluid is flowing into the patient at the prescribed rate.

Figure 4:
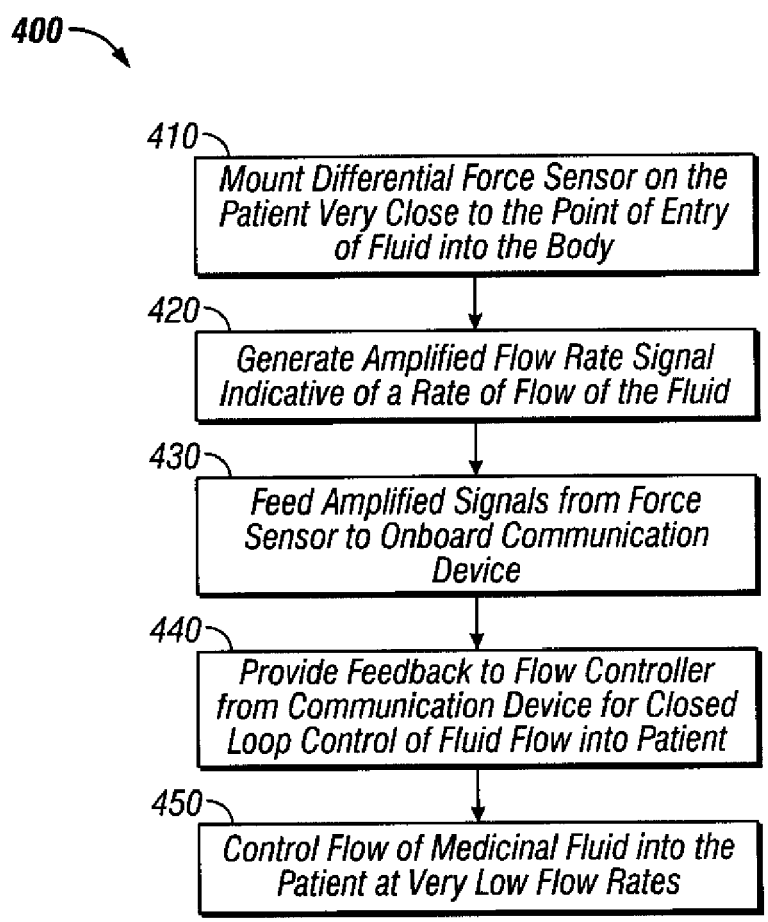
FIG. 4 illustrates a high level flow chart of operations illustrating logical operational steps of a method for measuring flow at a patient utilizing the differential force sensor of FIGS. 1-3, in accordance with an alternative embodiment.

FIG. 4 illustrates a high level flow chart of operations illustrating logical operational steps of a method 400 for measuring flow at a patient utilizing the differential force sensor 200, in accordance with an alternative embodiment. Again as reminder, in FIGS. 1-4, identical or similar parts or elements are generally indicated by identical reference numerals. FIG. 4 thus illustrates a variation to the previously depicted drawings of FIG. 1-3. The differential force sensor 200 can be mounted on the patient and very close to the point of entry into the body in order to read the flow closer to the patient, as depicted at block 410. The amplified flow rate signal indicative of a rate of flow of fluid can be generated, as depicted at block 420. The amplified signals from the differential force sensor 200 can be fed to the onboard communications device 340, as depicted at block 430. Thereafter, as illustrated at block 440, feedback can be provided to the flow controller 140 through the communication channel associated with the communication device 340. The communication channel is open to the fluid delivery system 100 and provides feedback to allow for closed loop control of the fluid flow into the patient. The flow of medicinal fluid into the patient can be controlled at very low flow rates and time required for the fluid to enter the patient can be minimized, as shown at block 450. Note that the method 400 described herein also can be configured for closed loop control of the fluid flow into the patient.

The differential force sensor 200 can be mounted on the patient very close to the point of entry into the body and allows for a fluid delivery system to read the flow closer to the patient and take out or minimize the compliance of all elements up to the patient's catheter. The placement of the differential force sensor 200 allows the fluid delivery system 100 to pump the fluid at a higher frequency until the flow rate is actually reached at the patient and then adjusts to the flow rate needed to ensure patient health. It is believed that by utilizing the system and approach described herein, the delivery system can precisely control the flow of the fluid into the patient at very low flow rates and minimizes the time required for the fluid to enter the patient. Note that in some embodiments the disclosed differential flow sensor can be implemented as a disposable pressure sensor.

It will be appreciated that variations of the above-disclosed and other features and functions, or alternatives thereof, may be desirably combined into many other different systems or applications. Also, that various presently unforeseen or unanticipated alternatives, modifications, variations or improvements therein may be subsequently made by those skilled in the art which are also intended to be encompassed by the following claims.

What is claimed is:

1. A system for controlling fluid flow that is delivered through a fluid line that enters a patient, the system comprising:
   a reduced cross-section orifice situated adjacent a point of entry of a fluid line into said patient;
   a differential force sensor including:
     a first force sensor;
     a second force sensor positioned adjacent the first force sensor;
     wherein said first force sensor is responsive to movement of a first flow diaphragm that is exposed to a first pressure in said fluid line upstream of the reduced cross-section orifice, and said second force sensor is responsive to movement of a second flow diaphragm that is exposed to a second pressure in the fluid line downstream of the reduced cross-section orifice;
     a first plunger associated with the first force sensor, wherein a first force exerted by movement of said first flow diaphragm in response to said first pressure is transferred to said first force sensor through said first plunger;
     a second plunger associated with the second force sensor, wherein a second force exerted by movement of said second flow diaphragm in response to said second pressure is transferred to said second force sensor through said second plunger; and
     said first force sensor and said second force sensor providing one or more sensor output signals;
   a flow controller that controls a rate of flow of said fluid through said fluid line; and
   one or more electronic devices, the one or more electronic devices responding to said one or more sensor output signals of said first force sensor and said second force sensor and providing one or more feedback signals to said flow controller, in a closed-loop manner, such that the flow controller actively controls the rate of flow of said fluid through said fluid line and into said patient.

2. The system of claim 1, wherein said one or more electronic devices are configured to perform signal processing on said one or more sensor output signals, wherein said signal processing includes performing a thermal compensation and/or a differential pressure calculation.

3. The system of claim 1, wherein said fluid comprises a medicinal fluid.

4. A system for controlling fluid flow that is delivered through a fluid line, comprising:
   a reduced cross-section orifice situated along the length of said fluid line;
   a first sense die and a second sense die positioned adjacent to one another, wherein said first sense die is responsive to movement of a first flow diaphragm that is exposed to a first pressure in said fluid line upstream of the reduced cross-section orifice, and said second sense die is responsive to movement of a second flow diaphragm that is exposed to a second pressure in the fluid line downstream of the reduced cross-section orifice, said first sense die and said second sense die providing one or more sensor output signals;
   a flow controller that controls a rate of flow of said fluid through said fluid line; and
   one or more electronic devices, the one or more electronic devices responding to said one or more sensor output signals of said first sense die and said second sense die and providing one or more feedback signals to said flow controller, in a closed-loop manner, such that said flow controller actively controls the rate of flow of said fluid through said fluid line.

5. The system of claim 4, wherein said reduced cross-section orifice situated adjacent a downstream end of said fluid line, and said downstream end of said fluid line is positioned within a patient, such that said reduced cross-section orifice is situated proximate a point of entry of said fluid line into said patient.

6. The system of claim 5, wherein said fluid comprises a medicinal fluid.

7. The system of claim 5, wherein said fluid comprises saline.

8. The system of claim 5, wherein said fluid comprises a nutritional fluid.

9. The system of claim 4, wherein said fluid controller causes the fluid flow to be initially conveyed at a higher rate of fluid flow until the fluid arrives adjacent to said reduced cross-section orifice, and then said fluid controller causes the fluid flow to be adjusted as needed to provide a desired lower rate of fluid flow through said fluid line.

10. The system of claim 4, wherein said one or more electronic devices are configured to performing signal processing on said one or more sensor output signals, wherein said signal processing includes performing a thermal compensation and/or a differential pressure calculation.

11. The system of claim 4, wherein said first sense die and said second sense die are housed in a common sensor package.

12. The system of claim 4, wherein said first sense die, said second sense die, and said one or more electronic devices are housed in a common sensor package.

13. The system of claim 4, further comprising:
   a first plunger associated with the first sense die, wherein a first force exerted by movement of said first flow diaphragm in response to said first pressure is transferred to said first sense die through said first plunger; and
   a second plunger associated with the second sense die, wherein a second force exerted by movement of said second flow diaphragm in response to said second pressure is transferred to said second sense die through said second plunger.

14. The system of claim 4, wherein:
   each of the first sense die and said second sense die is fixed relative to a printed circuit board;
   a housing is located over said first sense die and said second sense die;
   a first sensor orifice positioned directly adjacent said first sense die;
   a second sensor orifice positioned directly adjacent said second sense die; and a gel situated in said first sensor orifice and said second sensor orifice.

15. The system of claim 14, further comprising:
a first plunger associated with the first sense die, wherein a first force exerted by movement of said first flow diaphragm is transferred to said first sense die through said first plunger and said gel in said first sensor orifice; and
a second plunger associated with the second sense die, wherein a second force exerted by movement of said second flow diaphragm is transferred to said second sense die through said second plunger and said gel in said second sensor orifice.

16. A method for delivering a fluid into a patient, said method comprising:
providing a fluid line and a flow controller, wherein the fluid line includes a reduced cross-section orifice situated adjacent a point of entry of the fluid line into said patient;
providing a differential force sensor having a first force sensor and a second force sensor positioned adjacent to one another, wherein said first force sensor is responsive to movement of a first flow diaphragm that is exposed to a first pressure in said fluid line upstream of the reduced cross-section orifice, and said second force sensor is responsive to movement of a second flow diaphragm that is exposed to a second pressure in the fluid line downstream of the reduced cross-section orifice, said differential force sensor providing a measure of a flow rate of the fluid through the fluid line;
providing a feedback signal to the flow controller, wherein the feedback signal is related to the measure of the flow rate of the fluid provided by the differential force sensor; and
conveying said fluid from a reservoir to said patient through said fluid line, wherein said flow controller uses the feedback signal in a closed loop manner to actively control the flow rate of the fluid through said fluid line.

17. The method of claim 16 wherein said fluid includes a medicinal fluid.

18. The method of claim 16 wherein said fluid includes saline.

19. The method of claim 16 wherein said fluid includes a nutritional fluid.

20. The method of claim 16 further comprising initially conveying said fluid at a higher flow rate until the fluid arrives adjacent the point of entry of the fluid into the patient, wherein said flow rate is thereafter adjusted as needed to provide a lower desired flow rate of said fluid into said patient.

* * * * *